(12) United States Patent
Nakamura et al.

(10) Patent No.: US 6,987,022 B2
(45) Date of Patent: Jan. 17, 2006

(54) **LEUKEMIC CELL-ADSORBING MATERIAL CONTAINING LECTIN PROTEIN FROM *DOLICHOS* BEANS OR SOYBEANS**

(75) Inventors: Osamu Nakamura, Tosu (JP); Hideki Ohba, Kitakyushu (JP); Imre Sallay, Kyoto (JP); Fumio Yagi, Kagoshima (JP); Sawako Moriwaki, Shimada (JP); Seiji Yasuda, Tosu (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 363 days.

(21) Appl. No.: 10/158,157

(22) Filed: May 31, 2002

(65) Prior Publication Data

US 2002/0182209 A1 Dec. 5, 2002

Related U.S. Application Data

(63) Continuation-in-part of application No. 09/549,493, filed on Apr. 14, 2000, now Pat. No. 6,420,171.

(30) Foreign Application Priority Data

Nov. 30, 1999 (JP) ................................. 11-341164

(51) Int. Cl.
*C12N 5/06* (2006.01)
*C12N 5/08* (2006.01)
*C12N 11/10* (2006.01)
*C07K 17/02* (2006.01)
*C07K 17/10* (2006.01)

(52) U.S. Cl. ...................... 435/325; 435/177; 435/178; 435/261; 530/396; 530/402; 530/413; 530/812; 530/813

(58) Field of Classification Search ................ 435/325, 435/177, 178; 530/396, 402, 413, 812, 813
See application file for complete search history.

(56) References Cited

U.S. PATENT DOCUMENTS

| 4,403,037 A | * | 9/1983 | Coates .......................... 435/5 |
| 5,081,030 A | * | 1/1992 | Civin .......................... 435/380 |
| 6,420,171 B1 | * | 7/2002 | Nakamura et al. ........... 435/325 |

FOREIGN PATENT DOCUMENTS

JP 9-206096 * 8/1997

OTHER PUBLICATIONS

Hellstrom et al, The Juornal of Experimental Medicine, 1976, vol. 144, pp. 1381-1385.*

* cited by examiner

*Primary Examiner*—David M. Naff
(74) *Attorney, Agent, or Firm*—Wenderoth, Lind & Ponack, L.L.P.

(57) ABSTRACT

An efficient method for therapeutic treatment of a leukemic patient is disclosed in which the patient's body fluid under external circulation is brought into direct contact with an adsorbent material capable of adsorbing the leukemic cells in the body fluid specifically and selectively. The leukemic cell-adsorbent material, which is used by filling a column to form an adsorbent bed, is a conjugate of a lectin protein extracted from, e.g., *Dolichos* beans or soybeans coupled with a physiologically inert carrier material such as a polysaccharide in the form of beads or a superparamagnetic material in the form of iron oxide-based magnetic beads.

12 Claims, 3 Drawing Sheets

LEUKEMIC CELL-ADSORBING MATERIAL CONTAINING LECTIN PROTEIN FROM *DOLICHOS* BEANS OR SOYBEANS

This is a continuation-in-part application from a U.S. patent application Ser. No. 09/549,493 filed Apr. 14, 2000, now U.S. Pat. No. 6,420,171.

BACKGROUND OF THE INVENTION

The present invention relates to development of a suitable column to adsorb leukemic cells selectively from the blood of leukemic patients for the purpose of therapeutic treatment, and a leukemic cell-adsorbent material used therein.

The current therapeutic treatment of leukemia is to undertake transplantation of a healthy marrow following the administration of anticancer agents and radiation. Anticancer agents are administered until leukemic cells disappear in blood, which in general exhibit strong side effects to the patients of leukemia. They must endure a very severe life under the medical care for a quite long time. In addition, it is sometimes not certain that the relapse into the disease can be fully prevented even by a prolonged administration of anticancer agents.

On the other hand, a novel promising therapeutic way for leukemia has become highlighted by the discovery of lectin proteins derived from certain plants and animals which act as leukemic cell-capturing agents capable of recognizing leukemic cells specifically as reported in Japanese Patent Kokai 9-206096. This leukemic cell-capturing agent can discriminate leukemic cells from normal cells in the blood by recognizing the sugar chains expressed on the cancer cells specifically so that the lectin protein is expected to selectively remove leukemic cells from body fluids very efficiently.

It is a usual way to treat cancer patients by anticancer agents which are administrated either orally or parenterally to make the anticancer agents contact with the cancer cells through the circulatory blood system of the patient's body. A problem in this way is that the anticancer agents reach not only the target tissues but also other tissues in the whole body of the patient, because the anticancer agents are administered in a dose much larger than the actual desired dose for the target tissues after being diluted in blood stream over the whole body. Therefore, it is sometimes unavoidable that the body tissues other than the target tissues are subjected to unpredictably adverse side effects of the anticancer agents.

So far, attempts have been made repeatedly in order to develop a therapeutic treatment method by which the anticancer agents are concentrated to the target tissues as limitedly as possible to attack the cancer cells effectively. Unfortunately, however, no fully promising results have yet been obtained.

SUMMARY OF THE INVENTION

The primary object of the present invention is accordingly to provide a speedy and efficient means for the therapy of leukemia by bringing the leukemic cells in the externally circulating patient's body fluid into direct contact with a leukemic cell-capturing agent so as to remove the leukemic cells selectively from the body fluid of the patient.

The secondary object of the invention is to provide a novel leukemic cell-adsorbent material capable of capturing the leukemic cells selectively to remove the leukemic cells from the patient's body fluid, and to accomplish a rapid and reliable therapeutic result on the disease as well as an apparatus for leukemic cell adsorption.

Thus, the leukemic cell-adsorbent material provided by the present invention is a composite material which comprises:

(a) a leukemic cell-capturing agent which is a lectin protein derived from the body of a specific mushroom fungus such as *Agrocybe cylindracea* or a seed of a leguminous plant such as jequirity as well as, in particular, beans of *Dolichos biflorus*, referred to as *Dolichos* beans hereinafter, or beans of *Glycine max*, referred to as soybeans hereinafter; and (b) a physiologically inert carrier material supporting the leukemic cell-capturing agent as the component (a) by forming a chemical bonding therebetween.

The leukemic cell-adsorbing column provided by this invention is a tubular body made of an insoluble and physiologically inert material holding a bed of the leukemic cell-adsorbent material defined above therein.

DETAILED DESCRIPTION OF THE PREFERRED EMBODIMENTS

Figure 1:
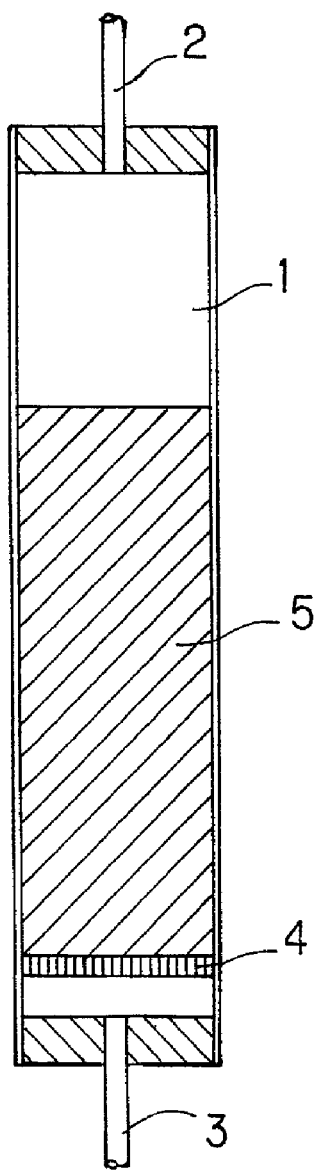
FIG. 1 is a schematic axial cross sectional view of the inventive leukemic cell-adsorbing column holding a bed of the leukemic cell-adsorbent material therein.

With an object to develop an efficient therapeutic means for the treatment of leukemia, the inventors have conducted extensive investigations and have arrived at an unexpected discovery that, since the leukemic cells of a patient are mostly found in the patient's blood, a remarkable therapeutic result could be accomplished by externally circulating the patient's blood and bringing the blood under circulation into direct contact with a leukemic cell-adsorbent material comprising a leukemic cell-capturing agent so as to have the leukemic cells adsorbed on the adsorbent material selectively leading to the establishment of the present invention after detailed studies on the adsorbent material and the leukemic cell-adsorbing apparatus utilizing the adsorbent material.

The leukemic cell-capturing agent comprised in the inventive leukemic cell-adsorbent material is a lectin protein derived from specific plants or animals occurring in nature. The source material, from which the lectin protein as the leukemic cell-capturing agent can be obtained, includes, on one hand, a body pulp of a specific mushroom fungus having a botanical name of *Agrocybe cylindracea* and called "yanagimatsutake" by the Japanese local name, or beans of a leguminous plant called jequirity beans having a botanical name of *Abrus precatorius* and called "touazuki" by the Japanese local name as well as, on the other hand, *Dolichos* beans or soybeans. All of their lectin proteins which can recognize leukemic cells can be applied to this inventive system.

The carrier material which supports the lectin protein mentioned above as the leukemic cell-capturing agent is not particularly limitative including inorganic and organic materials, any of which is suitable as the carrier material provided that the material has physiological inertness and sufficient affinity to the leukemic cell-capturing agent. The physiological inertness mentioned here implies that, when the material is contacted with a physiological body fluid such as blood and lymph as well as blood cells and lymphocytes, the material never causes denaturation against them or no noxious substance is leached out therefrom into the contacting body fluid, and further the performance of the contacting body fluid is not adversely affected thereby. A particularly preferable carrier material is a gelled polysaccharide compound such as galactan or a derivative thereof in the form of beads available on the market for use as a gel filtration agent under the trade names of Sepharoses (each a product by Amasham Pharmacia Biotech Co.). If the commercial beads product has a particle diameter of 250 to 350 $\mu$m, the beads as obtained can be used as a carrier material for the inventive adsorbent material.

Besides the above-mentioned polysaccharide beads as the carrier material of the inventive adsorbent material, particular advantages can be obtained by preparing the inventive adsorbent material by using magnetic beads as the carrier material with regard to easiness of handling and good binding efficiency of the lectin protein. A commercial product of such magnetic beads usable in the present invention is available on the market as sold under the tradename of, for example, Dynabeads M-450 Tosylactivated (a product by Dynal A.S., Norway). This product, having an average particle diameter of 2 to 5 $\mu$m, consists of super-paramagnetic iron oxide-based polystyrene beads having a cladding layer of a polyurethane resin of which the surface is activated by p-toluenesulfonyl chloride to provide reactive groups for covalent bond of proteins containing primary amino or thiol groups.

In the leukemic cell-adsorbent material of the invention, the lectin protein as the leukemic cell-capturing agent is bound to the carrier material described above by forming a chemical bonding. Namely, the leukemic cell-capturing agent is supported on the carrier material through covalent linkages.

Thus, the leukemic cell-adsorbent material is prepared by immersing the polysaccharide beads as a typical example of the carrier material in an aqueous hydrochloric acid solution to be swollen therewith followed by addition of the lectin protein and agitation of the mixture at room temperature for 1 to 5 hours to allow the reaction between the amino groups in the lectin protein and the functional groups in the polysaccharide compound such as imidocarbonate groups and cyanate ester groups to form isourea linkages through which the lectin protein is bound to the polysaccharide compound. Since not all of the functional groups in the polysaccharide compound are usually reacted with the lectin protein, the unreacted functional groups are preferably blocked by reacting with an amino acid such as glycine.

The leukemic cell-adsorbing column of the invention is prepared by filling a tubular body made of an insoluble material with the leukemic cell-adsorbent material described above, which is a conjugate of the leukemic cell-capturing agent and the carrier material, to form a bed of the adsorbent material. The insoluble material mentioned here implies that the material never affects the physiological performance of a body fluid such as blood and lymph as well as blood cells and lymphocytes which contact with the material, and that the material never releases any noxious substances into the fluid. Those materials used in artificial organs are generally suitable for the purpose including glass materials, plastic resins and corrosion-resistant metals without particular limitations. Although the cross sectional profile of the tubular body can be circular, rectangular, square or elliptic, it is usually convenient to employ a tube of a circular cross section as the body of the column. Assuming that the column body is made of a cylindrical tube having a circular cross section, the inner diameter of the column is in the range from 10 to 20 mm or, preferably, from 10 to 15 mm and the height of the column is in the range from 50 to 200 mm or, preferably, from 60 to 80 mm. If necessary, the dimensions can be increased.

A mesh screen sheet or a perforated plate with pores of 80 $\mu$m pore diameter is usually provided in the vicinity of the lower end of the column body to receive the adsorbent material forming a bed and to allow the body fluid cells pass through. It is preferable that the bed of the adsorbent material has a height of at least 20 mm.

In the following, the subject matter of the present invention and the performance thereof are described in more detail by making reference to the accompanying drawing.

FIG. 1 is a schematic axial cross sectional view of a typical example of the inventive leukemic cell-adsorbing column, in which the column body 1 is made of a cylindrical glass or plastic tube and provided at the top with a fluid introducing tube 2 and at the bottom with a fluid discharge tube 3. The column 1 is filled with a leukemic cell-adsorbent material 5 as supported on a filter plate 4 provided in the vicinity of the lower end of the column 1.

The blood taken by withdrawing from the blood vessel of a leukemic patient containing leukemic cells is introduced into the column 1 through the fluid inlet tube 2 after being freed from red blood cells by centrifugation and flows down through the bed 5 of the leukemic cell-adsorbent material where the blood is contacted with the leukemic cell-capturing agent to have the leukemic cells adsorbed selectively on the adsorbent material 5. The blood thus freed from the leukemic cells is discharged out of the fluid discharge tube 3 at the bottom of the column 1 and returned to the body of the patient. By continuing blood circulation in this way, the blood of a leukemic patient is freed from leukemic cells without affecting normal performance of the patient's blood adversely to exhibit a remarkable therapeutic effect with safety and reliability.

Figure 2:
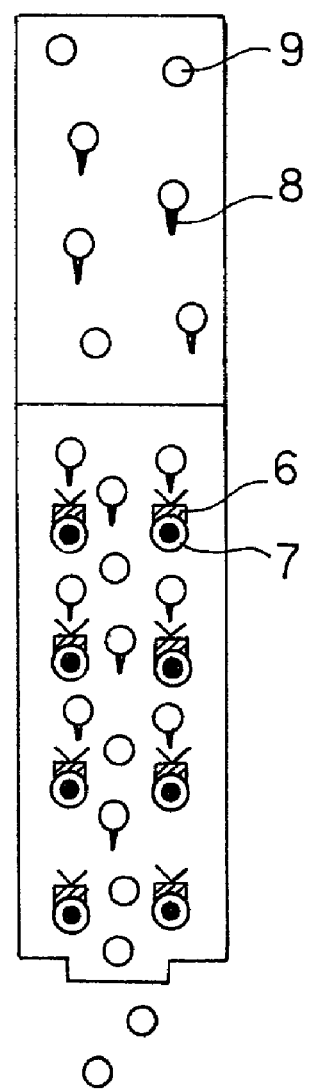
FIG. 2 is a schematic drawing to illustrate the presumable mechanism for the effectiveness of the inventive leukemic cell-adsorbent material for the selective adsorption of leukemic cells from a body fluid.

FIG. 2 is a schematic drawing to illustrate a possible mechanism for the effectiveness of the therapeutic treatment according to the present invention. Thus, when the blood of a leukemic patient containing leukemic cells 8 and normal cells 9 is introduced into the adsorbing column and passes through the bed of the adsorbent material formed from carrier beads 7 bearing a lectin protein as the leukemic cell-capturing agent 6 thereon, the leukemic cells 8 are selectively bound to the lectin protein and immobilized on the beads leaving the normal cells unadsorbed so that the blood discharged out of the fluid discharge tube at the bottom of the column is free from leukemic cells 8.

The leukemic cell-adsorbent material having leukemic cells adsorbed thereon by the treatment of a body fluid of a leukemic patient described above can be regenerated in the following manner and used repeatedly. Thus, if the adsorbent bed is washed with an aqueous solution of a saccharide compound, such as lactose, capable of recognizing the lectin protein specifically used in the adsorbent material, the leukemic cells are released from the adsorbent material, and thereafter the column gets ready for the next treatment.

In the following, the present invention is described in more detail by way of Examples, which, however, never limit the scope of the invention in any way.

EXAMPLE 1

A 1 g portion of Sepharose 6 MB (a product by Amasham Pharmacia Biotech Co.) was added to 100 ml of a 1 mM aqueous solution of hydrochloric acid and kept therein for 15 minutes to get swollen therewith followed by thorough rinse first with 200 ml of a 1 mM hydrochloric acid solution and then with 200 ml of a coupling buffer solution which was a 0.1 M aqueous solution of sodium hydrogencarbonate containing 0.5 N of sodium chloride and having a pH of 8.5.

In the next place, 3 mg of a lectin protein obtained from a pulp of yanagimatsutake, i.e. *Agrocybe cylindracea*, were dissolved in 5 ml of the same coupling buffer solution as used above, added into swollen Sepharose beads prepared as mentioned above as a carrier material, and agitated therein for 2 hours at 20° C. to couple the lectin protein with the carrier material giving 2.5 ml of a composite material thereof.

In the next place, the prepared composite material was washed three times alternately each time with 100 ml of a 0.1 N acetate buffer solution containing 0.5 N sodium chloride and having a pH of 4.5 and each time with a coupling buffer solution and then agitated in 30 ml of a 0.1 N aqueous solution of sodium hydrogencarbonate containing 0.2 N of glycine and having a pH of 8.5 for 2 hours at room temperature to block the unreacted functional groups in the carrier material followed by thorough rinse with a buffer solution for cell suspension to give 2.5 ml of a leukemic cell-adsorbent material.

EXAMPLE 2

A cylindrical glass or plastic column having an inner diameter of 12 mm and a height of 60 mm and provided with a mesh sheet of 80 μm pore diameter was filled with 2.5 ml of the leukemic cell-adsorbent material prepared in Example 1 to form a bed of the adsorbent material in a height of 20 mm to prepare a leukemic cell-adsorbing column.

T-cell series of Jurkat cells obtained from a patient of acute lymphatic leukemia were suspended in a phosphate-buffered physiological saline solution and the cell concentration of the suspension was adjusted to $1.5 \times 10^7$ cells/ml.

A 0.6 ml portion of the cell suspension was passed at 25° C. through the adsorbing column to have the leukemic cells bound to the lectin protein followed by thorough rinse with a phosphate-buffered physiological saline solution.

Figure 3:
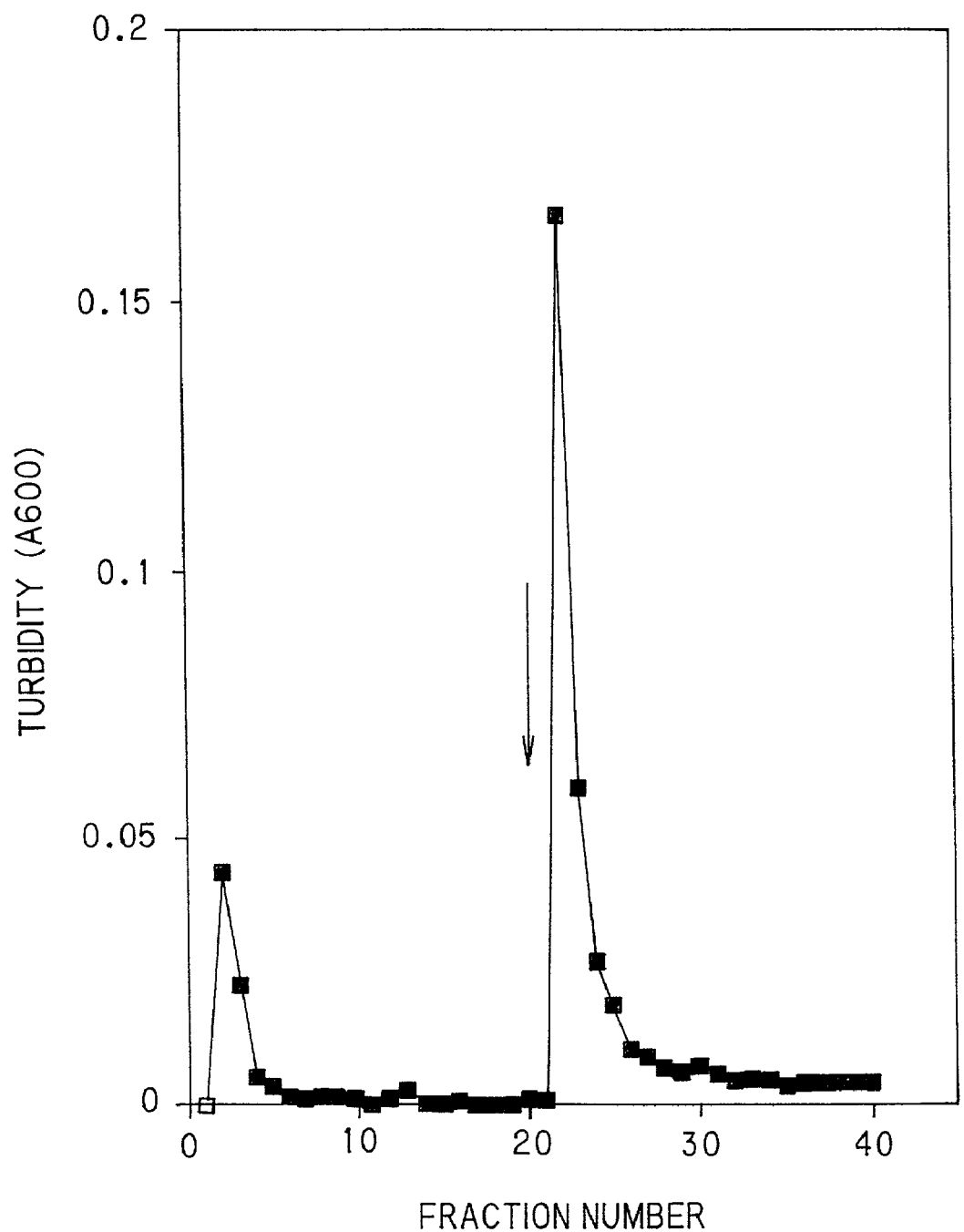
FIG. 3 is a graph showing the turbidity of the fractions obtained by elution in Example.

In the next place, elution of the adsorbing column bearing the leukemic cells was conducted by passing a 100 mM lactose solution in a phosphate-buffered physiological saline solution and the eluate solution was collected in fractions each having a volume of 1.5 ml. Each of the fractions was subjected to a photometric measurement of the turbidity (A600) to give the results graphically shown in FIG. 3.

The experimental results described above support the conclusion that the leukemic cells contained in blood can be adsorbed by the lectin protein in the leukemic cell-adsorbent material to be removed from the blood and the leukemic cells bound to the adsorbent material can be eluted out by elution with a lactose solution.

EXAMPLE 3

Figure 4:
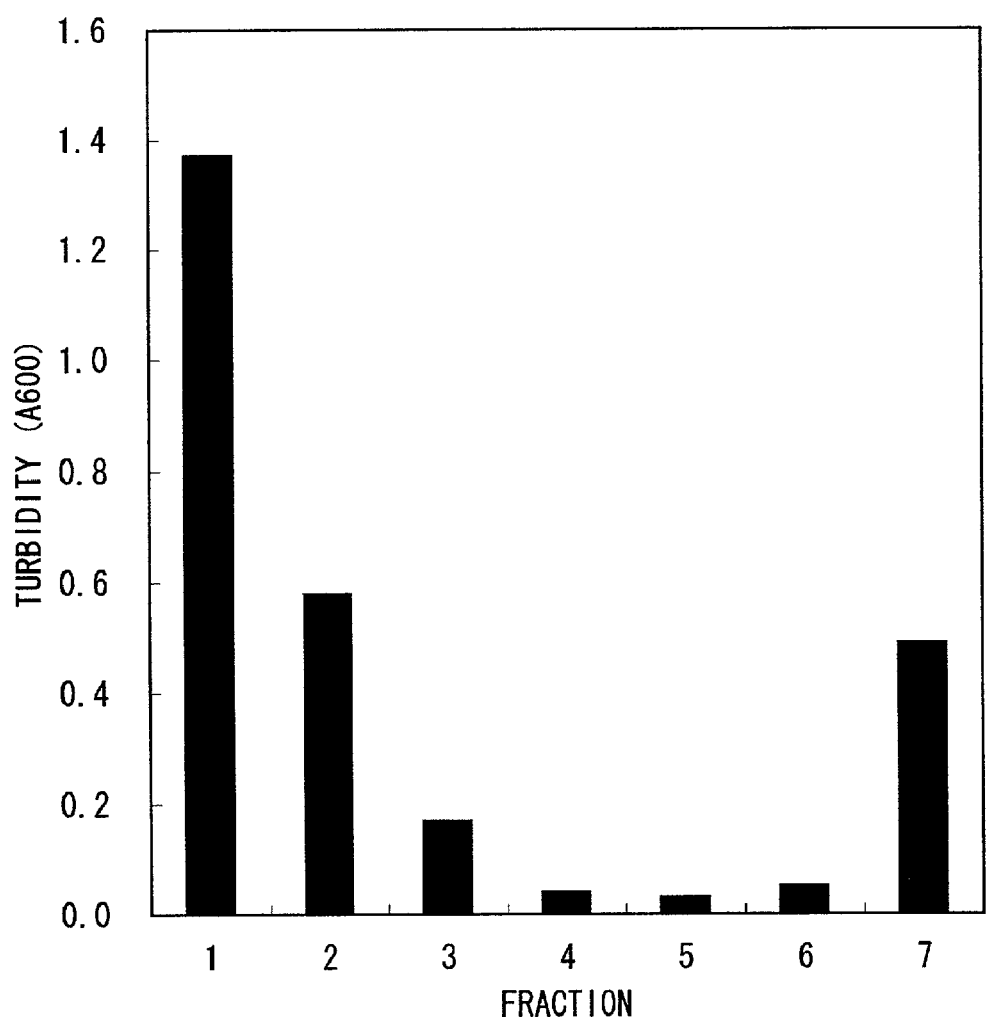
FIG. 4 is a bar chart showing the turbidity of eluate fractions in the separation of normal lymphocytes from Jurkat cells with magnetic beads conjugated with the lectin protein derived from *Dolichos* beans, referred to as DBA, in Example 3.

A mixed aqueous suspension of normal lymphocytes and Jurkat cells was subjected to a separation test by using conjugate beads bearing DBA, i.e. the lectin protein extracted from *Dolichos* beans by covalent bonding. The results of elution tests are shown in FIG. 4 by the bar chart indicating turbidity of the eluates in seven fractions 1 to 7, of which the fraction 1 is for the initial mixture of normal lymphocytes and Jurkat cells, fraction 2 is for the untrapped cells, fraction 3 is for the eluate with 100 mM lactose solution, fraction 4 is for the eluate with 200 mM lactose solution, fraction 5 is for the wash with PBS, fraction 6 is for the eluate with 100 mM D-GalNac solution and fraction 7 is for the eluate with 200 mM D-GalNac solution. Fractions 2 and 3 correspond to normal lymphocytes and fraction 7 corresponds to the Jurkat cells as identified by the flow cytometry. These results clearly indicate efficient separation of normal lymphocytes from Jurkat cells by using the DBA conjugate.

What is claimed is:

1. An adsorbent material for adsorption of leukemic cells which is a conjugate material comprising:
   (a) a lectin protein as a leukemic cell-capturing agent derived from *Dolichos* beans or soybeans; and
   (b) a physiologically inert carrier material which is a superparamagnetic material in the form of iron oxide-based magnetic beads having an average particle diameter in the range of 2 to 5 μm, said beads supporting the lectin protein as the component (a).

2. The adsorbent material for adsorption of leukemic cells as claimed in claim 1 in which the lectin protein is a lectin protein derived from *Dolichos* beans.

3. The adsorbent material for adsorption of leukemic cells as claimed in claim 1 in which the lectin protein is a lectin protein derived from soybeans.

4. The adsorbent material for adsorption of leukemic cells as claimed in claim 1 in which the lectin protein and the carrier material are bound by forming chemical linkages between amino groups which are present in the lectin protein and functional groups which are present in the carrier material.

5. The adsorbent material for adsorption of leukemic cells as claimed in claim 4 in which unreacted functional groups in the carrier material are blocked with an amino acid.

6. The adsorbent material for adsorption of leukemic cells as claimed in claim 5 in which the amino acid is glycine.

7. A leukemic cell-adsorbing column which comprises:
   (A) a tubular body made from a physiologically inert material; and
   (B) the leukemic cell-adsorbent material according to claim 1 filling the tubular body to form a bed of the adsorbent material.

8. The leukemic cell-adsorbing column as claimed in claim 7 in which the bed of the leukemic cell-adsorbent material has a height of at least 20 mm.

9. The leukemic cell-adsorbing column as claimed in claim 7 in which the tubular body has an inner diameter in the range from 10 to 20 mm and a height in the range from 50 to 200 mm.

10. The leukemic cell-adsorbing column as claimed in claim 7 which further comprises a mesh screen provided at or in the vicinity of the lower end of the tubular body of the column which supports the leukemic cell-adsorbent material thereon.

11. A method for selectively removing leukemic cells from a body fluid containing leukemic cells and normal cells which comprises the step of bringing the body fluid into contact with the leukemic cell-adsorbent material according to claim 1 to have the leukemic cells selectively adsorbed on the adsorbent material.

12. The method for selectively removing leukemic cells from a body fluid containing leukemic cells and normal cells as claimed in claim 11 in which a tubular body made from a physiologically inert material is filled with the leukemic cell-adsorbent material in the form of a bed and said body fluid is passed through said tubular body filled with said leukemic cell-adsorbent material.

* * * * *